US012715823B2

(12) United States Patent
Zimmermann et al.

(10) Patent No.: US 12,715,823 B2
(45) Date of Patent: Aug. 25, 2026

(54) CATALYST FOR EXOTHERMAL REACTIONS

(71) Applicant: MAX-PLANCK-GESELLSCHAFT ZUR FÖRDERUNG DER WISSENSCHAFTEN E.V., Munich (DE)

(72) Inventors: Ronny Tobias Zimmermann, Madgeburg (DE); Jens Bremer, Madgeburg (DE); Kai Sundmacher, Helmstedt (DE)

(73) Assignee: MAX-PLANCK-GESELLSCHAFT ZUR FORDERUNG DER WISSENSCHAFTEN E.V., Munich (DE)

( * ) Notice: Subject to any disclaimer, the term of this patent is extended or adjusted under 35 U.S.C. 154(b) by 663 days.

(21) Appl. No.: 17/612,343

(22) PCT Filed: May 20, 2020

(86) PCT No.: PCT/EP2020/064040
§ 371 (c)(1),
(2) Date: Nov. 18, 2021

(87) PCT Pub. No.: WO2020/234337
PCT Pub. Date: Nov. 26, 2020

(65) Prior Publication Data

US 2022/0266235 A1 Aug. 25, 2022

(30) Foreign Application Priority Data

May 21, 2019 (EP) .................................... 19175573

(51) Int. Cl.
*C07C 1/12* (2006.01)
*B01J 35/30* (2024.01)
(Continued)

(52) U.S. Cl.
CPC ............... *C07C 1/12* (2013.01); *B01J 35/398* (2024.01); *B01J 35/40* (2024.01); *B01J 35/53* (2024.01); *B01J 35/56* (2024.01); *B01J 35/651* (2024.01)

(58) Field of Classification Search
CPC ... B01J 35/04; B01J 35/51; B01J 35/56; B01J 35/651; B01J 35/50; B07C 1/12
See application file for complete search history.

(56) References Cited

U.S. PATENT DOCUMENTS 4,495,308 A * 1/1985 Gibson .................... B01J 35/60 502/355
6,211,255 B1 4/2001 Schanke et al.
(Continued)

FOREIGN PATENT DOCUMENTS

CA 1202070 A 3/1986
CN 108430628 A 8/2018
(Continued)

OTHER PUBLICATIONS

Porexpert "Determination of porosity" 2014. https://www.porexpert.com/help/index.html?determination_of_porosity.htm (Year: 2014).*
(Continued)

*Primary Examiner* — Richard M Rump
(74) *Attorney, Agent, or Firm* — Tarolli, Sundheim, Covell & Tummino LLP

(57) ABSTRACT

The invention relates to a molded body which comprises a catalytically active region and a porous coating which lies on the catalytically active region, wherein at least 75 wt. % of the catalytically active material lies in the catalytically active region, and the porosity and average pore diameter of the catalytically active region and the porous coating satisfy the following condition: $[\Theta_{PB}^{1.5} \times d_{PB} \times (dKB+150\text{ nm})]/[\Theta_{KB}^{1.5} \times d_{KB} \times (d_{PB}+150\text{ nm})]<1$.

14 Claims, 6 Drawing Sheets

Figure 1A:
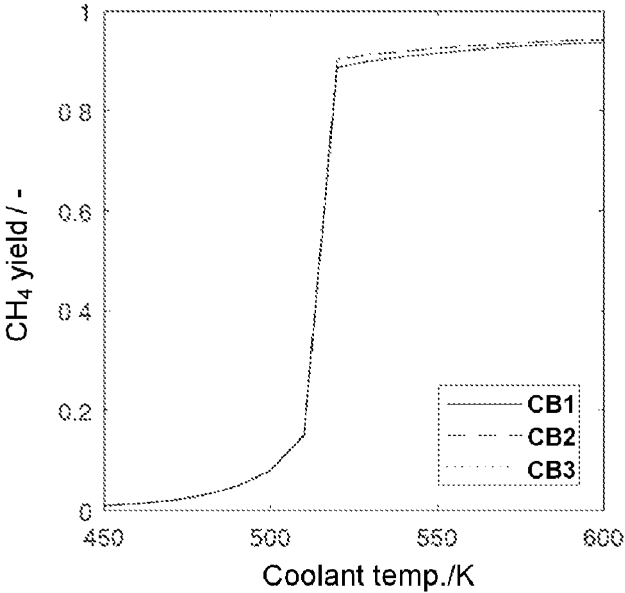

(51) Int. Cl.

| | |
|---|---|
| ***B01J 35/40*** | (2024.01) |
| ***B01J 35/53*** | (2024.01) |
| ***B01J 35/56*** | (2024.01) |
| ***B01J 35/64*** | (2024.01) |

(56) References Cited

U.S. PATENT DOCUMENTS

| | | | | |
|---|---|---|---|---|
| 6,426,316 | B2 * | 7/2002 | Tanaka | B01J 23/40 502/340 |
| 2009/0202885 | A1 | 8/2009 | Kim et al. | |
| 2010/0331171 | A1 | 12/2010 | Gajda et al. | |
| 2012/0198769 | A1 * | 8/2012 | Schirrmeister | C07C 51/215 977/773 |
| 2012/0302811 | A1 | 11/2012 | Long et al. | |
| 2019/0262803 | A1 * | 8/2019 | Yu | B01J 23/002 |

FOREIGN PATENT DOCUMENTS

| | | | | |
|---|---|---|---|---|
| DE | 2813329 | A1 | 10/1978 | |
| WO | 2011/045051 | A1 | 4/2011 | |
| WO | 2017161953 | A1 | 9/2017 | |
| WO | WO-2017209083 | A1 * | 12/2017 | B01D 46/0061 |

OTHER PUBLICATIONS

Applicant: Max-Planck-Gesellschaft Zur Förderung Der Wissenschaften e.V.; "Catalyst for Exothermal Reactions"; PCT International Patent Application No. PCT/EP2020/064040 Filed May 20, 2020; PCT International Search Report and Written Opinion; 15 pgs.

C.J. Brinker et al., Journal of Membrane Science, 94, 1994, pp. 85-102.

Froment, G. F. "Fixed bed catalytic reactors—current design status." Industrial & Engineering Chemistry 59.2 (1967): 18-27.

Hagen, J. "Catalyst shapes and production of heterogeneous catalysts." Industrial Catalysis 2 (2006): 223-239.

Harriott, Peter. "Thermal conductivity of catalyst pellets and other porous particles: Part I: Review of models and published results." The Chemical Engineering Journal 10.1 (1975): 65-71.

Hwang, Sungwon, and Robin Smith. "Optimum reactor design in methanation processes with nonuniform catalysts." Chemical Engineering Communications 196.5 (2008): 616-642.

Aguiar, P., et al. "Improving catalyst structures and reactor configurations for autothermal reaction systems: application to solid oxide fuel cells." Chemical Engineering Science 56.2 (2001): 651-658.

Deutschmann, Olaf, et al. "Heterogeneous catalysis and solid catalysts, 1. Fundamentals." Ullmann's encyclopedia of Industrial chemistry (2000).

Koschany, Franz, David Schlereth, and Olaf Hinrichsen. "On the kinetics of the methanation of carbon dioxide on coprecipitated NiAl (O) x." Applied Catalysis B: Environmental 181 (2016): 504-516.

Landau, Miron V. "Sol-Gel Process." Handbook of Heterogeneous Catalysis: Online vol. 1, Wiley-VCH Verlag; (2008): 119-160.

Martin, Holger, and Michael Nilles. "Radiale warmeleitung in durchstromten schüttungsrohren." Chemie Ingenieur Technik 65.12 (1993): 1468-1477; https://doi.org/10.1002/cite.330651206, Considered only on basis in ISR.

Schuth, F., & Hesse, M. (2008). Catalyst Forming. In G. Ertl, H. Knözinger, F. Schüth, & J. Weitkamp (Eds.), Handbook of Heterogeneous Catalysis (pp. 676-699). Weinheim: Wiley-VCH.

F. Schüth, "General Principles for the Synthesis and Modification of Porous Materials", pp. 622-629, in "Handbook of Porous Solids", Ed.: F. Schüth, S.W. Sing, J. Weitkamp, vol. 1, Wiley-VCH, 2002.

Wakao, N., and T. Funazkri. "Effect of fluid dispersion coefficients on particle-to-fluid mass transfer coefficients in packed beds: correlation of Sherwood numbers." Chemical Engineering Science 33.10 (1978): 1375-1384.

Yagi, Sakae, and Daizo Kunii. "Studies on effective thermal conductivities in packed beds." AlChE Journal 3.3 (1957): 373-381.

Chinese Application No. 202080036709.0, Office Action dated Oct. 28, 2023.

Yang, et al., "Influence of Geometry Factors of Chemical Regenerative Reactor", Building Energy & Environment, vol. 36, No. 2, Feb. 2017, 24-28.

* cited by examiner

CATALYST FOR EXOTHERMAL REACTIONS

The present invention relates to shaped catalyst bodies and the use thereof for exothermic gas-phase reactions.

Macroscopic shaped bodies having dimensions in the millimeter or centimeter range are usually employed for the catalysis of industrial processes. In fixed-bed reactors, pulverulent catalysts can lead to a severe pressure drop. An overview of customary shaped catalyst bodies for heterogeneous catalysis may be found, for example, in "Industrial Catalysis—A Practical Approach", chapter 6: "Catalyst Shapes and Production of Heterogeneous Catalysts", Author Jens Hagen, Wiley-VCH Verlag, 2006, and also "Heterogeneous Catalysis and Solid Catalysts", H. Knözinger et al., in Ullmann's Encyclopedia of Industrial Chemistry, Wiley-VCH Verlag, 2009.

Depending on the distribution of the catalytically active material in the shaped catalyst body, a distinction is made, for example, between a homogeneous structure, an "egg yolk" structure and an "egg shell" structure. In the homogeneous structure, the catalytically active material is distributed uniformly in the shaped body. In the egg yolk structure, the catalytically active material is present in the core of the shaped body and is surrounded by a catalytically inactive shell. In the egg shell structure, the shaped catalyst body has a catalytically inactive core which is surrounded by a catalytically active shell.

Many industrially important chemical processes involve an exothermic gas-phase reaction, for example a hydrogenation (e.g. a methanation), an oxidation, an acetylation, an amination or a nitrilation. A high space time yield is in principle sought here. On the other hand, in exothermic reactions there is a risk that "hot spots", i.e. local regions having a very high temperature, will be formed in the reactor; these hot spots can lead to damage to the catalyst.

An overview of methanation as one of the industrially relevant exothermic gas-phase reactions may be found in S. Rönsch et al., Fuel, 166, 2016, pp. 276-296. In methanation, carbon oxides (CO and/or $CO_2$) are reacted with hydrogen in a strongly exothermic reaction to form methane. The following reaction equation describes the reaction of $CO_2$ with hydrogen:

$$CO_2+4H_2 \rightarrow CH_4+2H_2O$$

Owing to thermodynamic restrictions, catalyst deactivation and safety aspects, various reactor concepts have been developed in order to be able to remove the heat liberated by heterogeneously catalyzed, exothermic reactions efficiently. A widespread concept involves fixed-bed tube reactors. These frequently consist of wall-cooled tubes which are filled with catalytically active shaped bodies. In general, many of these tubes are assembled to form a shell-and-tube reactor.

At elevated rates of liberation of heat, it is not possible, despite wall cooling, to operate these reactors without a pronounced hot spot, even at small tube diameters. However, pronounced hot spots should be avoided for the above-mentioned reasons and because of additional costs for materials which are resistant to high temperatures.

A known approach for avoiding hot spots is the injection of product gas or inert gas into the reactor feed. As a result of this dilution, the heat of reaction liberated is reduced and the temperature increase in the reactor is therefore decreased. A disadvantage of this procedure is the reduced space-time yield. Furthermore, dilution with inert gas requires a subsequent treatment of the product stream, which increases the process costs. In addition, dilution with product gas requires an additional compressor in order to compensate for the decrease in reactor pressure.

From an economic point of view, it is therefore advantageous to keep dilution of the reactants as small as possible. Various reactor concepts have been examined for this purpose. Examples are the use of a plurality of cooling zones, a plurality of adiabatic fixed-bed reactors in series, structured catalyst packings, catalyst dilution, membrane reactors or distributed feed gas injection. These concepts frequently require an increased outlay for manufacture.

Apart from the conventional steady-state mode of operation of reactors, the dynamic mode of operation of reactors has moved into the focus of research in the light of the energy crisis. Electric energy, which is by way of example obtained from solar and wind energy, has to be converted by "power-to-X" processes into chemical energy carriers. To avoid large temporary storages for intermediates, dynamic operation of fixed-bed reactors as a function of the availability of surplus energy is preferred. However, this gives rise to additional challenges in the operation of fixed-bed reactors, for example due to inverse behavior or hysteresis phenomena.

S. Hwang et al., Chem. Eng. Comm., 196, 2009, pp. 616-642, describe a shaped catalyst body for a hydrogen-rich methanation. Various shaped catalyst bodies having an inhomogeneous distribution of the catalytically active material are described in simulations. The shaped catalyst body has a homogeneous pore structure.

L. Kershenbaum et al., Chemical Engineering Science, 56, 2001, pp. 651-658, describe a system containing a ceramic oxide fuel cell and a reactor for steam reforming. In steam reforming, water is reacted with methane to form $CO/CO_2$ and hydrogen in a strongly endothermic reaction. The hydrogen can be fed to the fuel cell. A shaped catalyst body which has an outer catalytically inactive, porous coating surrounding the catalytically active region in the interior of the shaped body is described for the endothermic steam reforming. More precise details regarding the porosities and pore diameters in these different regions of the shaped catalyst body are not given.

It is an object of the present invention to provide efficient catalysis of exothermic reactions (e.g. methanation), with a very good compromise between high space-time yield and sufficiently low catalyst temperature (i.e. avoidance of "hot spots" which could damage the catalyst) being achieved. The catalyst should be suitable for industrial chemical processes and allow efficient operation of the reactor even under dynamic conditions and various load states.

The object is achieved by a shaped body which contains a catalytically active material and which comprises a catalytically active region and also a porous coating which is present on the catalytically active region, wherein at least 75% by weight of the catalytically active material of the shaped body are present in the catalytically active region and the porous coating and the catalytically active region satisfy the following condition:

$$[\Theta_{PB}^{1.5} \times d_{PB} \times (d_{KB}+150 \text{ nm})]/[\Theta_{KB}^{1.5} \times d_{KB} \times (d_{PB}+150 \text{ nm})] < 1.0,$$

where $\Theta_{PB}$ is the porosity of the porous coating;

$d_{PB}$ is the average pore diameter, in nm, of the porous coating;

$\Theta_{KB}$ is the porosity of the catalytically active region;

$d_{KB}$ is the average pore diameter, in nm, of the catalytically active region.

In the context of the present invention, it was recognized that in the case of an exothermic chemical reaction the presence of a porous and essentially catalytically inactive coating ("porous shell") which surrounds the catalytically active core of the shaped body has an advantageous influence on the catalyst temperature and at the same time keeps the space-time yield at a high or at least acceptable level. A further decrease in the catalyst temperature combined with sufficiently high space-time yields is realized when the porosities and average pore diameters of the catalytically active core and of the essentially catalytically inactive shell are matched to one another so that a chemical compound in the shell has a lower effective diffusion coefficient than in the core of the shaped body. The effective diffusion coefficient is a measure of the mobility of a compound in a porous material and can be set via the pore diameter and/or the porosity.

It has surprisingly been found in the context of the present invention that an improved compromise between high space-time yield and sufficiently low catalyst temperature (i.e. avoidance of "hot spots") is achieved in exothermic chemical reactions when the porosities and average pore diameters of the catalytically active core and the porous coating which surrounds the core and essentially does not contain any catalytically active material are matched to one another so that they satisfy the abovementioned relationship. i.e.

$$[\Theta_{PB}^{1.5}\times d_{PB}\times(d_{KB}+150\text{ nm})]/[\Theta_{KB}^{1.5}\times d_{KB}\times(d_{PB}+150\text{ nm})]<1.0.$$

For example, a catalytically active starting shaped body which is commercially available or is produced by standard methods known to a person skilled in the art functions as catalytically active region. The catalytically active material can, for example, be homogeneously distributed in the catalytically active starting shaped body. As an alternative, it is also possible for the catalytically active material to be inhomogenously distributed in the starting shaped body, for example in the form of an egg shell structure (i.e. a catalytic active shell which surrounds a catalytically inactive material). A porous coating which contains no or only very little catalytically active material is applied to this catalytically active starting shaped body. Taking into account the porosity and the average pore diameter of the catalytically active starting shaped body, porosity and average pore diameter of the porous coating applied to the starting shaped body are selected so that the abovementioned relationship is satisfied.

The catalytically active region comprises, for example, a porous support material on which the catalytically active material is dispersed. A person skilled in the art will know which catalytically active materials are suitable in each case for the exothermic chemical reaction to be carried out. As already indicated above, catalytically active starting shaped bodies which comprise a porous support material and a catalytically active material dispersed on this support material are commercially available and/or can be obtained by known production processes. An overview of the production of catalytically active shaped bodies may be found, for example, in the publication by F. Schoth, M. Hesse, "Catalyst Forming", in Handbook of Heterogeneous Catalysis, pp. 676-699, Wiley-VCH, Weinheim (2008), Ed.: G. Ertl, H. Knözinger. F. Schüth, J. Weitkamp.

Illustrative porous support materials which can be present in the catalytically active region are oxides (e.g. $Al_2O_3$ or $SiO_2$), nitrides, carbides and/or elemental carbon.

The catalytically active material is selected as a function of the exothermic reaction to be catalyzed. For example, mention may be made in this context of metals (e.g. transition metals) and transition metal oxides.

The catalytically active region of the shaped catalyst body of the invention has, for example, a porosity $\Theta_{KB}$ in the range from 0.2 to 0.8, more preferably from 0.3 to 0.7.

The average pore diameter $d_{KB}$ of the catalytically active region can vary over a relatively wide range. The catalytically active region can contain micropores, mesopores and/or macropores. According to the IUPAC definition, micropores have a diameter of <2 nm, mesopores have a diameter of from 2 to 50 nm and macropores have a diameter of >50 nm. For example, the catalytically active region has an average pore diameter $d_{KB}$ of from 1 nm to 2000 nm, more preferably from 2 nm to 1200 nm or from 2 nm to 500 nm.

On the basis of knowledge of the porosity and of the average pore diameter of the catalytically active starting shaped body, it is possible to select the porosity and the average pore diameter of the porous coating to be applied to the starting shaped body so that the following condition is satisfied in the shaped body of the present invention:

$$[\Theta_{PB}^{1.5}\times d_{PB}\times(d_{KB}+150\text{ nm})]/[\Theta_{KB}^{1.5}\times d_{KB}\times(d_{PB}+150\text{ nm})]<1.0$$

Preference is given to:

$$[\Theta_{PB}^{1.5}\times d_{PB}\times(d_{KB}+150\text{ nm})]/[\Theta_{KB}^{1.5}\times d_{KB}\times(d_{PB}+150\text{ nm})]\leq 0.75$$

or $$[\Theta_{PB}^{1.5}\times d_{PB}\times(d_{KB}+150\text{ nm})]/[\Theta_{KB}^{1.5}\times d_{KB}\times(d_{PB}+150\text{ nm})]\leq 0.5$$

Even greater preference is given to $$0.01<[\Theta_{PB}^{1.5}\times d_{PB}\times(d_{KB}+150\text{ nm})]/[\Theta_{KB}^{1.5}\times d_{KB}\times(d_{PB}+150\text{ nm})]<1.0$$

or $$0.01<[\Theta_{PB}^{1.5}\times d_{PB}\times(d_{KB}+150\text{ nm})]/[\Theta_{KB}^{1.5}\times d_{KB}\times(d_{PB}+150\text{ nm})]\leq 0.75$$

or $$0.01<[\Theta_{PB}^{1.5}\times d_{PB}\times(d_{KB}+150\text{ nm})]/[\Theta_{KB}^{1.5}\times d_{KB}\times(d_{PB}+150\text{ nm})]\leq 0.5$$

Suitable processes for producing porous coatings are known to a person skilled in the art. A person skilled in the art will also know the measures by means of which the porosity $\Theta_{PB}$ and the average pore diameter $d_{PB}$ of a porous coating can be influenced.

The porous coating can, for example, be produced by a sol-gel process. The production of porous materials by sol-gel processes is described, for example, in:

M. V. Landau, "Sol-Gel Process", pp. 119-160, in "*Handbook of heterogeneous catalysis",* 2008, Vol. 1, Wiley-VCH Verlag, C. J. Brinker et al., Journal of Membrane Science, 94, 1994, pp. 85-102.

F. Schüth, "General Principles for the Synthesis and Modification of Porous Materials". pp. 622-629, in "Handbook of Porous Solids", Ed.: F. Schoth, S. W. Sing, J. Weitkamp, Vol. 1, Wiley-VCH, 2002.

Furthermore, it is possible to produce the porous coating by spray coating. Spray coating can, for example, be carried out in a fluidized-bed chamber. Such coating methods are known to a person skilled in the art. For example, the component forming the catalytically active region (e.g. a porous support material on which the catalytically active material is dispersed) is fluidized in a fluidized-bed chamber and a suspension of a particulate material which forms the porous coating is sprayed into the fluidized-bed chamber. The suspension is finely atomized by the nozzle. The particulate material of the suspension which is sprayed in deposits on the catalytically active support material and forms the porous coating. The thickness of the applied porous coating can, for example, be varied via the duration of the coating process in the fluidized-bed chamber and the rate at which the suspension is sprayed in. After coating in the fluidized-bed chamber is complete, the shaped bodies can additionally be subjected to a thermal treatment. Pore diameter and/or porosity of the porous coating can be influenced by means of this thermal treatment. The pore diameter and/or the porosity can also be influenced by the particle size of the particulate material of the suspension which is sprayed in. The porosity may be able to be reduced by use of a nonporous filler material.

For the porous coating, it is possible to use materials as are also used for the support material in the catalytically active region. For example, the porous coating contains an oxide (e.g. $Al_2O_3$, $SiO_2$, an alkaline earth metal oxide such as magnesium oxide, a rare earth metal oxide such as cerium oxide), a nitride, a carbide and/or elemental carbon.

The porous coating is preferably the outermost coating of the shaped body, i.e. there is no further coating on top of the porous coating. The porous coating is preferably present directly on the catalytically active region. Furthermore, preference is given to at least 90%, more preferably at least 95%, of the area of the catalytically active region being enclosed by the porous coating. In a preferred embodiment, the catalytically active region is completely enclosed by the porous coating.

Since the shaped body is to be suitable as catalyst for industrial chemical processes in appropriate reactors (e.g. a fixed-bed reactor), its dimensions are preferably in the millimeter or centimeter range. The shaped body of the present invention preferably has a volume-equivalent sphere diameter in the range from 1.0 mm to 50 mm, more preferably from 1.0 to 20 mm. As is generally known, the volume-equivalent sphere diameter is the diameter of a sphere which has the same volume as the body under consideration.

The porous coating of the shaped body has, for example, a layer thickness in the range from 10 μm to 2000 μm, more preferably from 50 μm to 1000 μm. If a porous coating which is too thin is used, this can have an adverse effect on the catalyst temperature, while a porous coating which is too thick can have an adverse effect on the space-time yield.

In principle, porosity $\Theta_{PB}$ and average pore diameter $d_{PB}$ of the porous coating can be varied over a relatively wide range as long as the abovementioned condition, i.e.

$$[\Theta_{PB}^{1.5}\times d_{PB}\times(d_{KB}+150\text{ nm})]/[\Theta_{KB}^{1.5}\times d_{KB}\times(d_{PB}+150\text{ nm})]<1.0,$$

is satisfied. However, to prevent hot spot formation on the shaped catalyst body even more effectively, preference can be given for the purposes of the present invention to selecting the average pore diameter of the porous coating in such a way that predominantly Knudsen diffusion takes place in the pores. The porous coating of the shaped catalyst body has, for example, an average pore diameter $d_{PB}$ of ≤200 nm, more preferably ≤150 nm, even more preferably ≤50 nm. For example, the average pore diameter $d_{PB}$ is in the range from 2 nm to 200 nm, more preferably from 2 nm to 150 nm, even more preferably from 2 nm to 50 nm.

Preference is given to at least 85% by weight, even more preferably at least 95% by weight or even at least 99% by weight, of the catalytically active material of the shaped body being present in the catalytically active region. For the purposes of the present invention, it is also possible for the entire catalytically active material to be present in the catalytically active region.

The shaped body can have a geometry as is generally customary in the field of catalysis. For example, the shaped body is present in the form of a pellet, a sphere, a ring, a tablet, an extrudate, a cylinder, a sponge-like shaped body or a honeycomb shaped body.

The present invention further relates to the production of the above-described shaped body, wherein a porous coating is applied to a starting shaped body which contains a catalytically active material.

As mentioned above, the porous coating can, for example, be applied by a sol-gel process.

The present invention further provides for the use of the above-described shaped body as catalyst for an exothermic gas-phase reaction.

The exothermic reaction has, for example, a standard enthalpy of reaction $\Delta H° \leq -10$ kJ/mol, more preferably $\leq -50$ kJ/mol, even more preferably $\leq -100$ kJ/mol.

For example, the exothermic gas-phase reaction is a hydrogenation (e.g. a methanation), an oxidation, an acetylation, an amination or a nitrilation.

The present invention further provides a process for the exothermic reaction of gaseous reactants in a reactor, wherein the reactants are brought into contact with the shaped body described above.

Suitable reactors for carrying out exothermic gas-phase reactions are known to those skilled in the art. For example, the reactor is a fixed-bed reactor, a fluidized-bed reactor, a wall reactor, a membrane reactor, a microreactor, a honeycomb reactor or a plate reactor.

As already indicated above, the exothermic reaction of gaseous reactants is, for example, a hydrogenation (e.g. a methanation), an oxidation, an acetylation, an amination or a nitrilation. Knowing the reaction to be carried out, a person skilled in the art will know which reactants to use. For example, in the case of methanation, $H_2$ is reacted with $CO_2$ and/or CO to form methane.

The shaped body of the present invention makes it possible to achieve an improved compromise between a very high space-time yield and a sufficiently low catalyst temperature (i.e. avoidance of "hot spots") in exothermic reactions. If the exothermic gas-phase reaction is, for example, a methanation, the improved property profile of the catalyst makes it possible for the reactants $CO_2$ and $H_2$ to be fed undiluted in a molar ratio of $CO_2$:$H_2$ in the range from 1/3.5 to 1/4.5 into the reactor without undesirable hot spots being formed on the catalyst material. Furthermore, it is possible to operate the reactor not only in a steady-state manner but also with load changes in the methanation.

Measurement Methods

Average Pore Diameter and Porosity:

The determination of the average pore diameter (median) and the porosity is carried out using mercury porosimetry in accordance with ISO 15901-1:2016. In expanded porosimetry, not only the average pore diameter (as median) and the specific pore volume (i.e. pore volume per unit mass of the sample) but also the porosity are determined. Here, the apparent density is firstly determined by means of pycnometry (e.g. mercury pycnometry). The porosity is then calculated as follows:

Porosity=specific pore volume×apparent density

For the porosimetric determination, the porous coating is, for example, separated from the catalytically active region and the two components are then measured separately.

EXAMPLES

Example of the Production of a Shaped Catalyst Body According to the Invention

The production of a shaped body according to the invention will be illustrated in detail with the aid of this example.

The Catalytically Active Region of the Shaped Body

Porous $\gamma$-$Al_2O_3$ balls having a sphere diameter of 2.5 mm (commercially available from Sasol) were impregnated with 9% by weight of nickel oxide. The porous $\gamma$-$Al_2O_3$ balls function as porous support material on which the catalytically active material (nickel oxide) is dispersed.

The average pore diameter $d_{KB}$ and the porosity $\Theta_{KB}$ of the $\gamma$-$Al_2O_3$ balls laden with nickel oxide were determined by mercury porosimetry. The porosity $\Theta_{KB}$ was 0.687 and the average pore diameter $d_{KB}$ was 10.7 nm.

Application of a Porous Coating to the Catalytically Active Region

In the shaped bodies according to the invention, the porous coating and the catalytically active region surrounded by this coating satisfy the following condition:

$$[\Theta_{PB}^{1.5}\times d_{PB}\times(d_{KB}+150\text{ nm})]/[\Theta_{KB}^{1.5}\times d_{KB}\times(d_{PB}+150\text{ nm})]<1.0$$

where $\Theta_{PB}$ is the porosity of the porous coating;

$d_{PB}$ is the average pore diameter, in nm, of the porous coating;

$\Theta_{KB}$ is the porosity of the catalytically active region;

$d_{KB}$ is the average pore diameter, in nm, of the catalytically active region.

Taking into account the porosity $\Theta_{KB}$ and the average pore diameter $d_{KB}$ of the above-described catalytically active region ($\Theta_{KB}$=0.687; $d_{KB}$=10.7 nm), the porosity $\Theta_{PB}$ and the average pore diameter $d_{PB}$ of the porous coating to be applied have to be selected so that the condition according to the invention is satisfied.

When a rather low porosity of 40%, for example, is selected for the porous coating, the average pore diameter of the porous coating must not exceed a value of 26.4 nm. As an alternative, when a relatively high porosity of 70% is selected for the porous coating, the average pore diameter of the porous coating must not exceed a value of 10.4 nm.

In the present example, a porous $Al_2O_3$ coating was applied by spray coating in a fluidized-bed chamber. As an alternative, coatings having a defined pore diameter and a defined porosity can also be applied by a sol-gel process as is known in principle to a person skilled in the art.

In the fluidized-bed chamber (diameter: 200 mm), the above-described nickel oxide-containing $\gamma$-$Al_2O_3$ balls were fluidized using air as fluidizing gas (temperature of the fluidizing gas introduced into the chamber: about 100° C.). An aqueous suspension of colloidal boehmite particles (i.e. colloidal AlO(OH) particles) was subsequently sprayed into the fluidized-bed chamber. The suspension sprayed in was finely atomized by the nozzle and the boehmite particles deposited on the surface of the $\gamma$-$Al_2O_3$ balls.

After 60 minutes, coated $\gamma$-$Al_2O_3$ balls were taken from the fluidized-bed chamber. These coated balls were subsequently subjected to a thermal treatment at 550° C. for three hours.

The porous coating had a thickness of about 105 μm. The porosity $\Theta_{PB}$ and the average pore diameter $d_{PB}$ of the porous coating applied to the $\gamma$-$Al_2O_3$ balls were determined by mercury porosimetry. The porosity $\Theta_{PB}$ was 0.282 and the average pore diameter $d_{PB}$ was 4.4 nm.

The properties of the shaped bodies produced in this example are summarized again below.

The $\gamma$-$Al_2O_3$ balls (sphere diameter: 2.5 mm) laden with nickel oxide in each case function as catalytically active region of the shaped bodies. The porosity $\Theta_{KB}$ and average pore diameter $d_{KB}$ of these balls had the following values:

$\Theta_{KB}$=0.687

$d_{KB}$=10.7 nm

These $\gamma$-$Al_2O_3$ balls laden with nickel oxide were provided with a porous aluminum oxide coating by spray coating in a fluidized-bed chamber (layer thickness of the porous coating: about 105 μm). No catalytically active material is present in this porous coating. The porosity $\Theta_{PB}$ and the average pore diameter $d_{PB}$ of the porous, catalytically inert coating had the following values:

$\Theta_{PB}$=0.282

$d_{PB}$=4.4 nm

The relationship $$[\Theta_{PB}^{1.5}\times d_{PB}\times(d_{KB}+150\text{ nm})]/[\Theta_{KB}^{1.5}\times d_{KB}\times(d_{PB}+150\text{ nm})]$$

gives a value of 0.11.

The average pore diameter $d_{PB}$ and the porosity $\Theta_{PB}$ of the porous coating applied were thus matched to the average pore diameter $d_{KB}$ and the porosity $\Theta_{KB}$ of the initially charged $Al_2O_3$ balls laden with nickel oxide in such a way that the relationship according to the invention is satisfied.

Properties of Shaped Catalyst Bodies in an Exothermic Reaction

In the inventive examples IB1 to IB6 and the comparative examples CB1 to CB5 described below, it is demonstrated by means of computer-aided simulations that the hot spot behavior is significantly improved in a strong exothermic reaction (while maintaining very high or at least sufficiently high space-time yields) when a catalytically inert porous coating is applied to a starting shaped body containing the catalytically active material and taking into account the porosity and the average pore diameter of the catalytically active core, the porosity and the average pore diameter of the porous coating are selected so that the following condition is satisfied:

$$[\Theta_{PB}^{1.5}\times d_{PB}\times(d_{KB}+150\text{ nm})]/[\Theta_{KB}^{1.5}\times d_{KB}\times(d_{PB}+150\text{ nm})]<1$$

where $\Theta_{PB}$ is the porosity of the porous coating;

$d_{PB}$ is the average pore diameter, in nm, of the porous coating;

$\Theta_{KB}$ is the porosity of the catalytically active region;

$d_{KB}$ is the average pore diameter, in nm, of the catalytically active region.

As an example of a strongly exothermic reaction, methanation (reaction of $CO_2$ with hydrogen to form methane) was simulated in a wall-cooled fixed-bed tube reactor. In the simulation, identical reactor and process conditions were used as a basis for all examples. The examples differ merely in respect of the shaped catalyst body.

The basis of the simulations is a heterogeneous model of a wall-cooled fixed-bed tube reactor which reproduces the state of the reactor along the tube axis and along the radius of the catalytically active shaped bodies (here balls). The state of the reactor is described here by the concentration of all chemical species and the temperature. The following assumptions and equations form the basis of the model:

- no pressure gradients in the reactor,
- no axial dispersion and heat conduction in the reactor,
- ideal gas behavior,
- constant coolant temperature,
- constant wall heat transfer coefficient on the outside of the reactor tube,
- heat transport resistance of the reactor wall is disregarded,
- wall heat transfer coefficient on the tube inside is calculated by the correlation of Martin and Nilles, see H. Martin and M. Nilles, *Chemie Ingenieur Technik,* 65(12):1468-1477, 1993.
- effective radial heat conduction in the fixed bed is calculated by the correlation of Yagi and Kunii, see S. Yagi and D Kunii, AIChE Journal, 3(3):373-381, 1957,
- effective radial heat conduction and wall heat transfer coefficient on the tube inside are summarized by the method of Froment, see G. F. Froment, Industrial & Engineering Chemistry, 59(2):18-27, 1967,
- thermal conductivity of the fixed bed calculated using known data and equations,
- mass transfer coefficients and heat transfer coefficients at the catalytically active shaped bodies are calculated by the method of N. Wakao et al., Chemical Engineering Science, 33(10):1375-1384, 1978,
- mass transport into the catalytically active shaped bodies is calculated according to Fick's first law,
- heat transport into the shaped catalyst bodies is calculated according to Fourier's law,
- effective thermal conductivity of the shaped catalyst bodies is derived from the model of Harriot, see P. Harriott, The Chemical Engineering Journal, 10(1):65-71, 1975.

The reaction kinetics of the methanation of $CO_2$ is described by Koschany et al., Applied Catalysis B: Environmental, 181, 2016, pp. 504-516. The catalytic activity of the shaped bodies is identical in all examples in the absence of transport resistances. The model was entered into the commercial calculation program Matlab and solved by means of the Newton solver of the CasADi Toolbox.

The model parameters used in the simulation are listed below:

- tube length: 1.5 m
- tube diameter: 3 cm
- diameter of the spherical shaped catalyst bodies: 2.5 mm
- proportion of voids in the fixed bed: 0.4
- wall heat transfer coefficient on outside of the tube: 500 $W/(m^2*K)$
- coolant temperature: 500 K
- gas entry velocity: 1 m/s
- reactor pressure: 5 bar
- thermal conductivity of solid: 2.5 W/(mK)
- molar proportion of hydrogen on the inlet side: 0.8
- molar proportion of carbon dioxide on the inlet side: 0.2
- temperature at the inlet side: 500 K The Shaped Catalyst Bodies of Comparative Examples CB1-CB5 and of the Inventive Examples IB1 to IB6

In the comparative examples CB1-CB3, the catalytically active material is homogeneously distributed in the shaped bodies.

Figure 1B:
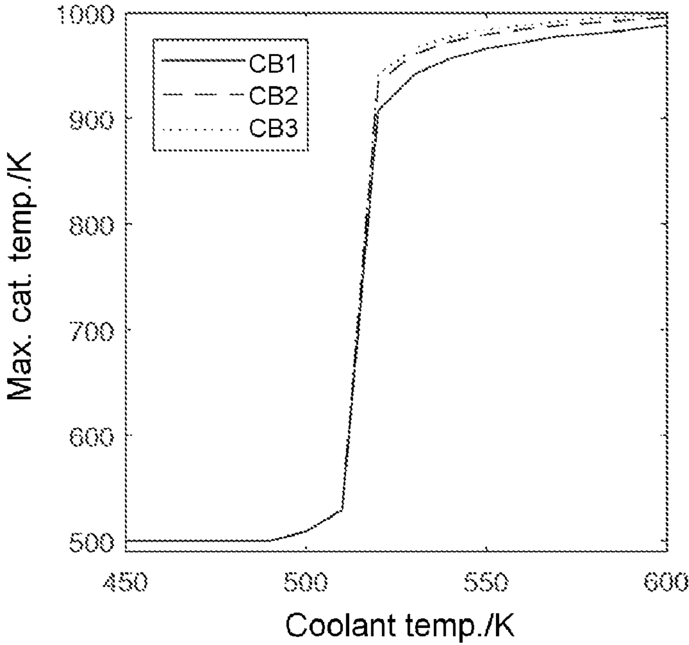

For CB1-CB3, FIG. 1*a* shows the methane yield as a function of the coolant temperature, while FIG. 1*b* shows the maximum catalyst temperature as a function of the coolant temperature.

In comparative example CB4 and the inventive examples IB1 to IB3, the shaped catalyst body has an egg yolk structure in each case, i.e. a catalytically active region is surrounded by a porous, catalytically inert shell. CB4 and IB1-IB3 have an identical catalytically active core. Furthermore, the porous coating enclosing the catalytically active core in CB4 and IB1-IB3 has the same average pore diameter $d_{PB}$ in each case. Only the porosity $\Theta_{PB}$ of the porous coating is varied. While the porosity $\Theta_{PB}$ of the shell is selected so that the condition $$[\Theta_{PB}^{1.5} \times d_{PB} \times (d_{KB}+150\text{ nm})]/[\Theta_{KB}^{1.5} \times d_{KB} \times (d_{PB}+150\text{ nm})]<1$$

is satisfied in IB1 to IB3, this does not apply in the case of the comparative example CB4.

Figure 2A:
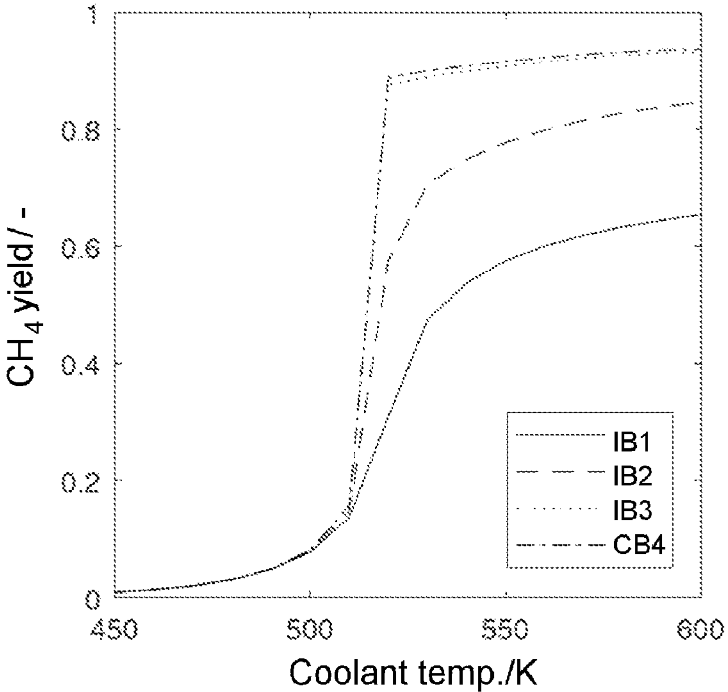
Figure 2B:
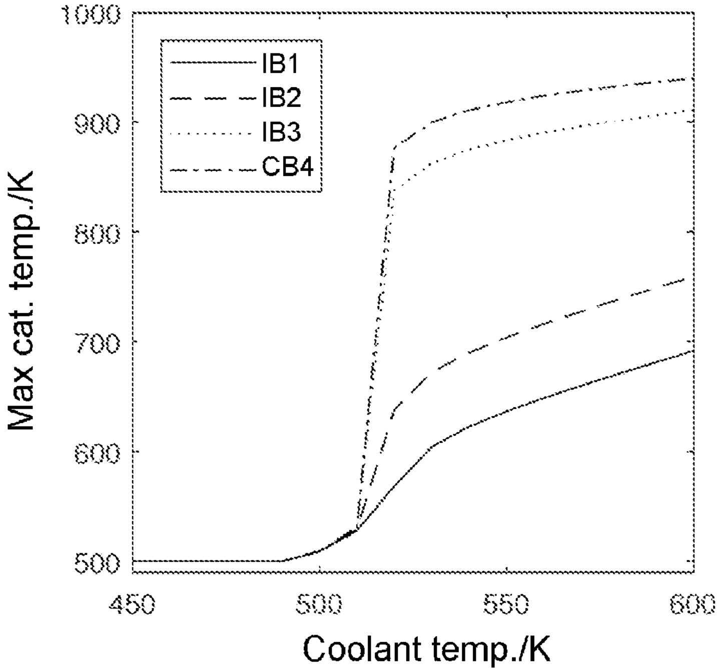

FIG. 2*a* shows the methane yield as a function of the coolant temperature for CB4 and IB1-IB3, while FIG. 2*b* shows the maximum catalyst temperature as a function of the coolant temperature.

In comparative example CB5 and the inventive examples IB4 to IB6, too, the shaped catalyst body in each case has an egg yolk structure, i.e. a catalytically active region is surrounded by a porous, catalytically inert coating. CB5 and IB4-IB6 have an identical catalytically active core. Furthermore, the porous coating enclosing the catalytically active core in CB5 and IB4-IB6 has the same porosity $\Theta_{PB}$ in each case. Only the average pore diameter $d_{PB}$ of the porous coating is varied. While the average pore diameter $d_{PB}$ of the porous coating is selected so that the condition $$[\Theta_{PB}^{1.5} \times d_{PB} \times (d_{KB}+150\text{ nm})]/[\Theta_{KB}^{1.5} \times d_{KB} \times (d_{PB}+150\text{ nm})]<1$$

is satisfied in IB4 to IB6, this does not apply in the case of comparative example CB5.

Figure 3A:
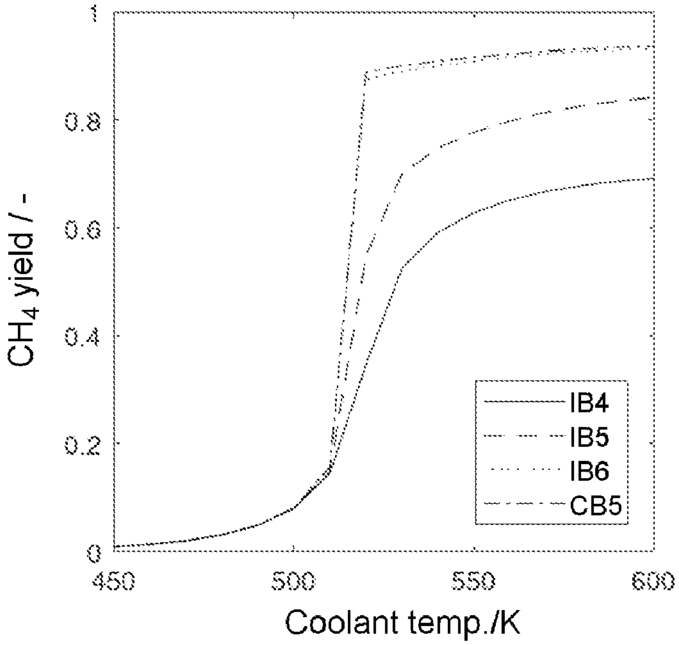
Figure 3B:
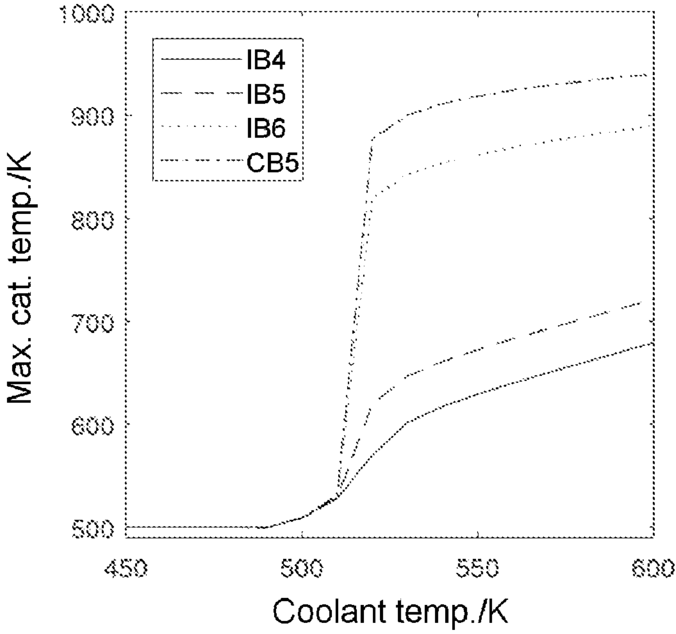

For CB5 and IB4-IB6, FIG. 3*a* shows the methane yield as a function of the coolant temperature, while FIG. 3*b* shows the maximum catalyst temperature as a function of the coolant temperature.

The properties of the shaped catalyst bodies are summarized in tables 1a and 1b below.

TABLE 1a

Properties of the shaped catalyst bodies

| | | Porous coating | | Catalytically active core | |
|---|---|---|---|---|---|
| Ex. | Catalytically active material | Porosity | Average pore diameter [nm] | Porosity | Average pore diameter [nm] |
| CB1 | Homogeneously distributed | — | — | 0.15 | 1000 |
| CB2 | Homogeneously distributed | — | — | 0.45 | 1000 |
| CB3 | Homogeneously distributed | — | — | 0.75 | 1000 |
| CB4 | Inhomogeneously distributed, egg yolk | 0.45 | 1000 | 0.45 | 1000 |
| IB1 | Inhomogeneously distributed, egg yolk | 0.06 | 1000 | 0.45 | 1000 |
| IB2 | Inhomogeneously distributed, egg yolk | 0.1 | 1000 | 0.45 | 1000 |

TABLE 1a-continued

Properties of the shaped catalyst bodies

| | | Porous coating | | Catalytically active core | |
|---|---|---|---|---|---|
| Ex. | Catalytically active material | Porosity | Average pore diameter [nm] | Porosity | Average pore diameter [nm] |
| IB3 | Inhomogeneously distributed, egg yolk | 0.3 | 1000 | 0.45 | 1000 |
| CB5 | Inhomogeneously distributed, egg yolk | 0.45 | 1000 | 0.45 | 1000 |
| IB4 | Inhomogeneously distributed, egg yolk | 0.45 | 5 | 0.45 | 1000 |
| IB5 | inhomogeneously distributed, egg yolk | 0.45 | 10 | 0.45 | 1000 |
| IB6 | Inhomogeneously distributed, egg yolk | 0.45 | 100 | 0.45 | 1000 |

TABLE 1b

Properties of the shaped catalyst bodies

| Ex. | $[\Theta_{PB}^{1.5} \times d_{PB} \times (d_{KB} + 150\text{ nm})]/[\Theta_{KB}^{1.5} \times d_{KB} \times (d_{PB} + 150\text{ nm})]$ |
|---|---|
| CB1 | — |
| CB2 | — |
| CB3 | — |
| CB4 | 1.0 |
| IB1 | 0.05 |
| IB2 | 0.1 |
| IB3 | 0.54 |
| CB5 | 1.0 |
| IB4 | 0.04 |
| IB5 | 0.07 |
| IB6 | 0.46 |

In FIG. 1*a*, the yield of $CH_4$ at the reactor outlet is plotted against the coolant temperature and in FIG. 1*b* the associated, maximum temperature of the shaped catalyst body in the reactor is plotted against the coolant temperature. Low maximum shaped body temperatures are also present at low coolant temperatures. However, owing to the low temperatures, the yield of $CH_4$ in the reactor is also low. Due to the strongly nonlinear dependence of the reaction rate on the temperature (Arrhenius equation), the conversion in the reactor increases greatly above a coolant temperature of about 515 K and a product yield of more than 80% is achieved. However, owing to the liberation of heat by the reaction, this high product yield is accompanied by a very large increase in the maximum shaped body temperature. Variation of the porosity has only a very small influence on the maximum temperature of the shaped catalyst body.

Owing to the very high maximum temperature of the shaped body, damage to the catalyst or a significantly shortened life of the catalyst has to be expected in CB1-CB3.

Comparison of comparative example CB4 in FIG. 2*a/b* and comparative example CB5 in FIG. 3*a/b* with the comparative examples CB1-CB3 in FIG. 1*a/b* indicates the following:

The presence of a porous, catalytically inert coating on the catalytically active core leads to a decrease in the maximum temperature of the shaped body, while the methane yield can continue to be maintained at a very high level.

The following can be concluded from the inventive examples IB1-IB3 and the comparative example CB4 in FIG. 2*a/b:*

If the porosity $\Theta_{PB}$ of the porous coating is reduced further so that $$[\Theta_{PB}^{1.5} \times d_{PB} \times (d_{KB}+150\text{ nm})]/[\Theta_{KB}^{1.5} \times d_{KB} \times (d_{PB}+150\text{ nm})]<1.0,$$

a further decrease in the maximum temperature of the shaped catalyst body also occurs.

In the inventive examples IB1 and IB2, a significant decrease in the temperature of the shaped catalyst body takes place, which in turn leads to a drastic increase in the catalyst life. Both IB1 and IB2 display still satisfactorily high methane yields. Although the decrease in the temperature of the shaped body is smaller in the inventive example IB3 than in IB1 and IB2, the methane yield can in return be kept at a very high level.

The following can be concluded from the inventive examples IB4-IB6 and the comparative example CB5 in FIG. 3*a/b:*

If the average pore diameter $d_{PB}$ of the porous coating is reduced further so that $$[\Theta_{PB}^{1.5} \times d_{PB} \times (d_{KB}+150\text{ nm})]/[\Theta_{KB}^{1.5} \times d_{KB} \times (d_{PB}+150\text{ nm})]<1.0,$$

a further decrease in the maximum temperature of the shaped catalyst body also occurs.

In the inventive examples IB4 and IB5, a significant decrease in the temperature of the shaped catalyst body takes place, which in turn leads to a drastic increase in the catalyst life. Both IB4 and IB5 display still sufficiently high methane yields. Although the decrease in the temperature of the shaped catalyst body is lower in the inventive example IB6 than in IB4 and IB5, the methane yield can in return be kept at a very high level.

The invention claimed is:

1. A shaped body which contains a catalytically active material, the shaped body comprising: a catalytically active region and a porous coating which is present on the catalytically active region, wherein:

the entire catalytically active material of the shaped body is present in the catalytically active region on which the porous coating is present, wherein the porous coating is the outermost coating of the shaped body, and wherein the porous coating is catalytically inactive, and the porous coating and the catalytically active region satisfy the following condition:

$$[\Theta_{PB}^{1.5} \times d_{PB} \times (d_{KB}+150\text{ nm})]/[\Theta_{KB}^{1.5} \times d_{KB} \times (d_{PB}+150\text{ nm})]<1.0$$

where:

$\Theta_{PB}$ is the porosity of the porous coating;

$d_{PB}$ is the average pore diameter, in nm, of the porous coating;

$\Theta_{KB}$ is the porosity of the catalytically active region;

$d_{KB}$ is the average pore diameter, in nm, of the catalytically active region.

2. The shaped body as claimed in claim 1, wherein the catalytically active region contains a porous support material on which the catalytically active material is dispersed.

3. The shaped body as claimed in claim 1, wherein the porosity $\Theta_{KB}$ of the catalytically active region is from 0.2 to 0.8.

4. The shaped body as claimed in claim 1, wherein the porosities and average pore diameters of the catalytically active region and of the porous coating present thereon satisfy the following condition:

$$0.01<[\Theta_{PB}^{1.5}\times d_{PB}\times(d_{KB}+150\text{ nm})]/[\Theta_{KB}^{1.5}\times d_{KB}\times(d_{PB}+150\text{ nm})]\leq 0.75.$$

5. The shaped body as claimed in claim 1, wherein the porous coating contains an oxide, a nitride, a carbide and/or elemental carbon.

6. The shaped body as claimed in claim 1, wherein the shaped body has a volume-equivalent sphere diameter in the range from 1.0 mm to 50 mm and/or the shaped body is present in the form of a pellet, a sphere, a ring, a tablet, an extrudate, a cylinder, a sponge-like shaped body or a honeycomb shaped body.

7. The shaped body as claimed in claim 1, wherein the porous coating of the shaped body has a layer thickness in the range from 10 μm to 2000 μm.

8. The shaped body as claimed in claim 1, wherein the average pore diameter $d_{PB}$ of the porous coating is ≤200 nm.

9. A catalyst for an exothermic gas-phase reaction comprising: the shaped body as claimed in claim 1.

10. The catalyst as claimed in claim 9, wherein the exothermic gas-phase reaction has a standard enthalpy of reaction ΔH° of ≤−10 kJ/mol.

11. A process for the exothermic reaction of gaseous reactants, the process comprising:

bringing the reactants into contact with the shaped body as claimed in claim 1 in a reactor.

12. The process as claimed in claim 11, wherein the reactor is a fixed-bed reactor, a fluidized-bed reactor, a wall reactor, a membrane reactor, a microreactor, a honeycomb reactor or a plate reactor.

13. The process as claimed in claim 11, wherein the exothermic reaction of gaseous reactants is a hydrogenation, an oxidation, an acetylation, an amination or a nitrilation.

14. The process as claimed as claim 13, wherein the hydrogenation is a methanation.

* * * * *